US00PP35453P2

(12) United States Plant Patent
Lim

(10) Patent No.: US PP35,453 P2
(45) Date of Patent: Nov. 7, 2023

(54) FLORIBUNDA SHRUB ROSE PLANT NAMED 'ALTSENSATION'

(50) Latin Name: *Rosa hybrida*
Varietal Denomination: ALTsensation

(71) Applicant: Altman Specialty Plants Inc., Vista, CA (US)

(72) Inventor: Peter Lim, Escondido, CA (US)

(73) Assignee: Altman Specialty Plants Inc, Vista, CA (US)

( * ) Notice: Subject to any disclaimer, the term of this patent is extended or adjusted under 35 U.S.C. 154(b) by 0 days.

(21) Appl. No.: 18/091,767

(22) Filed: Dec. 30, 2022

(51) Int. Cl.
*A01H 5/02* (2018.01)
*A01H 6/74* (2018.01)

(52) U.S. Cl.
USPC ..... Plt./102

(58) Field of Classification Search
USPC ..... Plt./102, 107, 141, 148, 149
CPC ... A01H 5/02; A01H 5/00; A01H 6/74; A01H 6/749
See application file for complete search history.

(56) References Cited

U.S. PATENT DOCUMENTS

PP11,836 P2 * 4/2001 Radler ..... A01H 5/02 Plt./108
PP29,167 P2 * 4/2018 Zlesak ..... A01H 5/02 Plt./149

OTHER PUBLICATIONS

North Carolina Extension Gardener Plant Toolbox *Rosa hybrida* 'Radrazz' PP#11836, retrieved on Apr. 12, 2023 at https://plants.ces.ncsu.edu/plants/rosa-hybrida-radrazz-pp-11836/, 5 pp. (Year: 2023).*

* cited by examiner

*Primary Examiner* — June Hwu
(74) *Attorney, Agent, or Firm* — Cassandra Bright

(57) ABSTRACT

A new and distinct cultivar of *Rosa* plant named 'ALTsensation' is disclosed, characterized by early blooming, double magenta pink flowers with a tea rose fragrance. Plants are vigorous and can be grown on their own roots. Plants are compact, flower continuously and exhibit good resistance to blackspot disease. The new variety is a *Rosa*, normally produced as an outdoor garden or container plant.

1 Drawing Sheet

Latin name of the genus and species: *Rosa hybrida.*
Variety denomination: 'ALTsensation'.

BACKGROUND OF THE INVENTION

The new *Rosa* cultivar is a product of a planned breeding program conducted by the inventor, Peter Ping Lim. The objective of the breeding program was to produce vigorous new garden rose varieties with continuous blooming for ornamental commercial applications. The cross resulting in this new variety was made during June of 2014.

The seed parent is the unpatented variety *Rosa* 'Francis Dubreuil'. The pollen parent is *Rosa* 'Radrazz' U.S. Plant Pat. No. 11,836. The new variety was selected in July of 2015 by the inventor in a group of seedlings resulting from the 2014 crossing, in a nursery in Vista, Calif.

Asexual reproduction of the new cultivar has been performed by vegetative cuttings. This was first performed at a research greenhouse in Vista, Calif. in July of 2015 and has shown that the unique features of this cultivar are stable and reproduced true to type in more than 5 successive generations.

SUMMARY OF THE INVENTION

The cultivar 'ALTsensation' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ALTsensation' These characteristics in combination distinguish 'ALTsensation' as a new and distinct *Rosa* cultivar:

1. Double, magenta pink flowers.
2. Strong tea rose fragrance.
3. Early prolific blooming.
4. Dark glossy foliage resistant to black spot and powdery mildew diseases.
5. Continuous flowering.
6. Compact plant.
7. Plants can be grown on their own roots; grafting is not required.

PARENT COMPARISONS

Plants of the new cultivar 'ALTsensation' are similar to plants of the seed parent, in most horticultural characteristics, however, plants of the new cultivar 'ALTsensation' differ in the following:

1. Flowers of the new cultivar are a rich pink color, while flowers of the seed parent are a dark red color.
2. Petal count of the new variety is higher than petal count of the seed parent.
3. Plant size of the new variety is smaller than plant size of this comparator.

Plants of the new cultivar 'ALTsensation' are similar to plants of the pollen parent in most horticultural characteristics, however, plants of the new cultivar 'ALTsensation' differs in the following;

1. Upper surface petal color of the new variety is Red-Purple N66A flushed Red-Purple N74A; upper surface petal color of the pollen parent is between Red 53C and Red 53D.
2. Petal count of the new variety is higher than petal count of the pollen parent.

COMMERCIAL COMPARISONS

Plants of the new cultivar 'ALTsensation' can be compared to the commercial variety *Rosa* 'Limkiss', U.S. Plant Pat. No. 28,929. These varieties are similar in most horticultural characteristics, however 'ALTsensation' differs in the following:

1. The new variety produces more flowers than plants of this comparator.
2. Flowers of the new variety have a strong tea rose fragrance, while flowers of this comparator have a strong spicy fragrance.
3. Foliage of the new variety is darker green than foliage of this comparator.

Plants of the new cultivar 'ALTsensation' can also be compared to the commercial variety *Rosa* 'JACtourn', U.S. Plant Pat. No. 16,498. These varieties are similar in most horticultural characteristics, however 'ALTsensation' differs in the following:

1. Flowers of the new variety produce more petals than flowers of this comparator.
2. Flowers of the new variety are magenta pink, while flowers of this comparator are dark red.
3. Plants of the new variety are smaller than plants of this comparator.

BRIEF DESCRIPTION OF THE PHOTOGRAPH

The accompanying photograph illustrates in full color a close up of an individual flower. The photograph was taken using conventional techniques and although colors may appear different from actual colors due to light reflectance it is as accurate as possible by conventional photographic techniques

DETAILED BOTANICAL DESCRIPTION

In the following description, color references are made to The Royal Horticultural Society Colour Chart 2007 except where general terms of ordinary dictionary significance are used. The following observations and measurements describe 'ALTsensation' plants grown outdoors, in Palm Desert, Calif. The growing temperature ranged from approximately 10° C. to 38° C. during the day and from approximately 5° C. to 22° C. during the night. Measurements were taken in September. General light conditions were very bright, normal sunlight. Measurements and numerical values represent averages of typical plant types. Botanical classification: *Rosa* 'ALTsensation'.

*Market classification*.—Floribunda shrub rose.

PROPAGATION

Time to initiate roots: About 15 days at approximately 20° C.

Time to produce a rooted cutting: About 35 days at approximately 20° C.

PLANT

Age of plant described: Approximately 1.5 years.
Growth habit: Compact.
Container size: 2 gallon.
Height: 32 cm.
Plant spread: 50 cm.
Rootstock: Own root.
Growth rate: Moderate.
Branching characteristics: Sympodial branching.
Length of primary lateral branches: Average range 18 to 45 cm.
Diameter of Lateral Branches: Approximately 6 mm to 7 mm.
Quantity branches: 6 to 8 main branches, moderate lateral branches, 6 to 10 lateral branches per main branch.
Branches-young wood:
*Diameter*.—Approximately 4 mm.
*Texture*.—Glabrous, sparse minute, soft, short thorns.
*Approximately density/quantity of prickles*.—Sparse.
*Color*.—Near RHS Yellow-Green 152C. Faint flush of Greyed-Red 181B.
Branches-old wood:
*Diameter*.—Approximately 5 to 9 mm.
*Color*.—Near Yellow-Green 144A. Oldest section has longitudinal scales colored near Grey 201C.
*Texture*.—Glabrous. Oldest, basal growth scaly.
*Thorns*.—
*Approximately density/quantity of thorns*.—Young growth: Sparse, soft thorns which disappear with maturity. Approximately 1 mm in diameter and 2 to 3 mm long. Colored near RHS Greyed-Orange N172A. Mature growth: Moderately dense, apiculate thorns about 13 mm at base, 8 mm to 10 mm long. Colored near RHS Grey-Orange 166A. Not hooked.

FOLIAGE

Leaf:
*Arrangement*.—Alternate and compound.
*Quantity*.—Average 6 to 10 per main branch.
*Internode*.—Average range 3 cm to 5 cm.
*Average length*.—Approximately 9 cm.
*Average width*.—Approximately 6 cm.
Rachis:
*Average length*.—Approximately 3 cm to 6 cm.
*Average diameter*.—Approximately 2 mm.
*Color*.—Upper surface: Near RHS Yellow-Green 144C. Lower surface: Near RHS Yellow-Green 144B.
*Texture*.—Glabrous all surfaces.
Leaflet:
*Quantity*.—5 or 7 per leaf, most commonly 5.
*Average length*.—Approximately 3 cm.
*Average width*.—Approximately 2.5 cm.
*Shape of blade*.—Broad ovate.
*Apex*.—Acute.
*Base*.—Broadly rounded.
*Margin*.—Finely serrate.
*Appearance of top surface*.—Moderately glossy.
*Appearance of bottom surface*.—Matte.
*Texture of top surface*.—Glabrous.
*Texture of bottom surface*.—Glabrous.

*Color*.—Young foliage upper side: Near RHS Green 137C. Young foliage under side: Near RHS Green 138B. Mature foliage upper side: Near RHS Green 139A. Mature foliage under side: Near RHS Green 137C.

*Venation*.—Type: Reticulate. Venation color upper side: Near RHS Yellow-Green 144C. Venation color under side: Near RHS Yellow-Green 144B.

Petiole:

*Average length*.—Approximately 1.5 cm to 3.0 cm.

*Average diameter*.—Approximately 3 mm.

*Color*.—Upper surface: Near RHS Yellow-Green 144C. Lower surface: Near RHS Yellow-Green 144B.

*Petiole wing*.—Typically 15 mm long and 5 mm wide. Apex apiculate. Upper surface colored near RHS Yellow-Green 144C, lower surface colored near Yellow-Green 145B.

*Texture*.—Glabrous.

FLOWER

Natural flowering season: Spring until Autumn.

Inflorescence type and habit: 3 to 5 flowers typically clustered together.

Rate of flower opening: Approximately 7 days from bud to fully opened flower.

Flower longevity on plant: 10 to 14 days, after fully opened.

Quantity of flowers: 20 to 30 fully opened flowers and buds.

Flower description: Fully double rotate.

Flower shape:

*From above*.—Round to very slightly irregular round.

*Profile of upper part of flower*.—Flattened convex.

*Profile of lower part of flower*.—Flattened convex.

Flower size:

*Diameter*.—Approximately 8 cm.

*Height*.—Approximately 5.5 cm.

Peduncle:

*Length*.—2.5 cm.

*Diameter*.—4 mm.

*Color*.—Near RHS Yellow-Green 144A.

*Texture*.—Softly prickly.

Petals:

*Petal arrangement*.—Multiple rotate, overlapping whorls.

*Petal quantity*.—Average 50 to 65.

*Length*.—3.5 cm.

*Width*.—4 cm.

*Shape*.—Obovate.

*Margin*.—Entire.

*Apex*.—Cordate single short notch at apex.

*Base*.—Very broad attenuate.

*Texture*.—Glabrous all surfaces.

*Color*.—When opening: Upper surface: Near RHS Red-Purple N66A flushed Red-Purple N74A. Lower surface: Near RHS Red-Purple 67B. Fully opened: Upper surface: Near RHS Red-Purple N74A. Lower surface: Near RHS Red-Purple N74B.

Bud:

*Shape*.—Ovate.

*Length*.—Approximately 3 cm.

*Diameter*.—Approximately 1.8 cm.

*Color*.—Near RHS Red-Purple N66A.

Sepals:

*Quantity*.—5.

*Length*.—2 cm.

*Width*.—9 mm.

*Shape*.—Deltoid.

*Apex*.—Apiculate.

*Margin*.—Entire.

*Texture*.—Slightly pubescent lower surface, glabrous upper surface.

*Color*.—Interior Surface: Near RHS Green 138C, flushed 137B. Exterior Surface: Near RHS Green 138B.

Receptacle:

*Length*.—9 mm.

*Width*.—12 mm.

*Shape*.—Flat.

*Color*.—Near RHS Green 145C.

Fragrance: Strong tea rose scent.

REPRODUCTIVE ORGANS

Stamens:

*Quantity*.—About 20.

*Filament length*.—Approximately 6 mm to 8 mm.

*Filament color*.—Near RHS Yellow-White 158D, upper section near Red-Purple 63B.

Anthers:

*Length*.—3 mm.

*Shape*.—Oblate.

*Color*.—Near RHS Red-Purple 61A.

*Pollen*.—None observed.

Pistil: Not observed.

OTHER CHARACTERISTICS

Seeds and fruits: Not observed.

Disease/pest resistance: Good overall disease resistance to normal pests and diseases typical of garden roses. Very good resistance to blackspot (*Diplocarpon rosae*). Very good resistance to powdery mildew (*Podosphaera pannosa*). In a three-year confidential field trial of floribunda shrub roses the new variety 'ALTsensation' remains free of powdery mildew year-round while varieties planted nearby were showed symptoms of powdery mildew.

What is claimed is:

1. A new and distinct cultivar of floribunda shrub rose plant named 'ALTsensation' as herein illustrated and described.

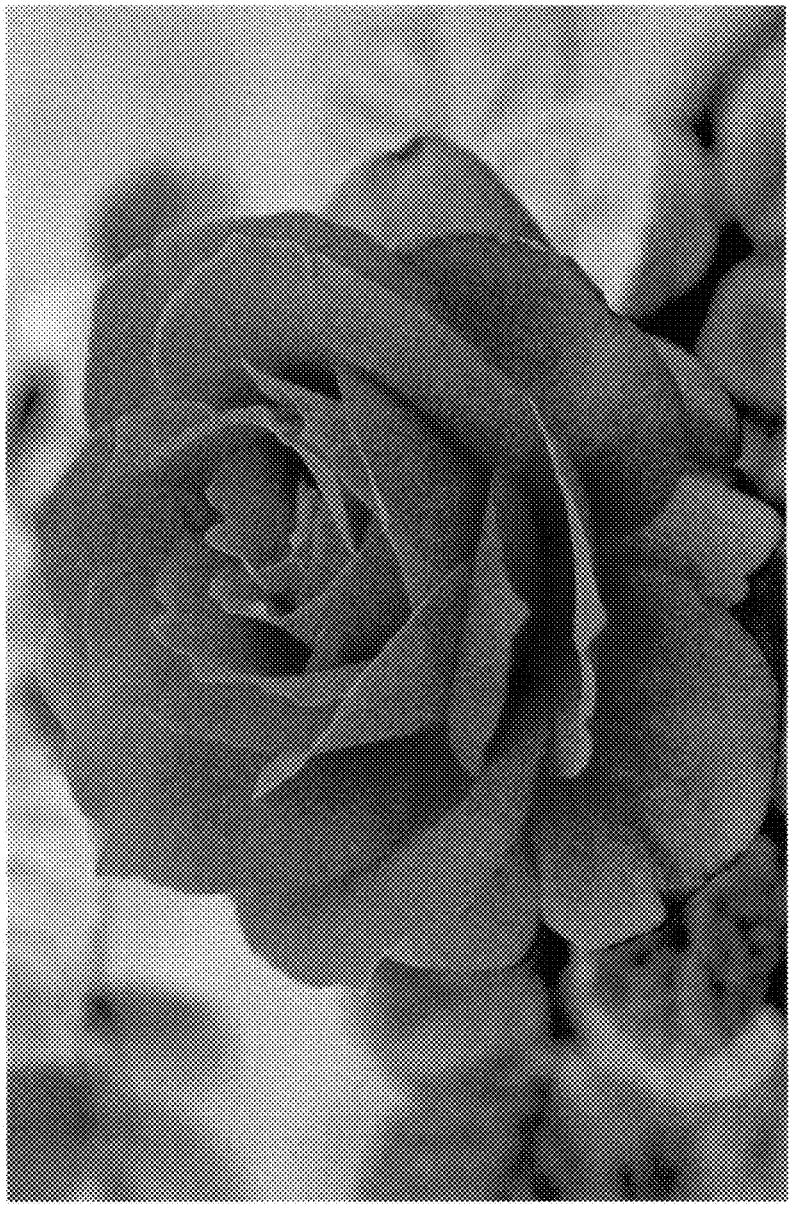

* * * * *